(12) United States Patent
Slavin

(10) Patent No.: US 9,457,195 B2
(45) Date of Patent: Oct. 4, 2016

(54) IMPLANTABLE MEDICAL DEVICE

(71) Applicant: Konstantin V. Slavin, Oak Park, IL (US)

(72) Inventor: Konstantin V. Slavin, Oak Park, IL (US)

(*) Notice: Subject to any disclaimer, the term of this patent is extended or adjusted under 35 U.S.C. 154(b) by 0 days.

(21) Appl. No.: 14/152,494

(22) Filed: Jan. 10, 2014

(65) Prior Publication Data

US 2014/0194953 A1 Jul. 10, 2014

Related U.S. Application Data

(60) Provisional application No. 61/751,030, filed on Jan. 10, 2013.

(51) Int. Cl.
*A61N 1/36* (2006.01)
*A61N 1/375* (2006.01)
*A61N 1/378* (2006.01)

(52) U.S. Cl.
CPC .............. *A61N 1/375* (2013.01); *A61N 1/3605* (2013.01); *A61N 1/378* (2013.01); *A61N 1/3752* (2013.01)

(58) Field of Classification Search
CPC ............................ A61N 1/375; A61N 1/3752
USPC ........................................ 607/36–38
See application file for complete search history.

(56) References Cited

U.S. PATENT DOCUMENTS

| | | | |
|---|---|---|---|
| 5,411,538 A * | 5/1995 | Lin | 607/33 |
| 7,590,454 B2 | 9/2009 | Garabedian et al. | |
| 7,894,906 B2 | 2/2011 | Shuros | |
| 8,082,039 B2 | 12/2011 | Kim et al. | |
| 2011/0022100 A1 | 1/2011 | Brase et al. | |
| 2012/0130438 A1* | 5/2012 | Seeley et al. | 607/2 |

* cited by examiner

*Primary Examiner* — Paula J Stice
(74) *Attorney, Agent, or Firm* — Michael Best & Friedrich LLP

(57) ABSTRACT

An implantable medical device including a first generator. The first generator includes a first power source coupled to a first controller. The first header is removably coupled to the first generator and includes a first lead configuration. The device includes a first lead with a lead body having first terminals and at least one electrode on an end opposite the first terminals. The first terminals are removably received and secured by the first lead configuration of the first header and configured to communicate with the first generator.

20 Claims, 7 Drawing Sheets

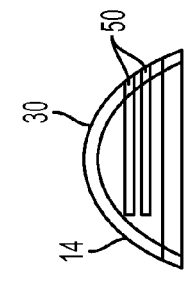
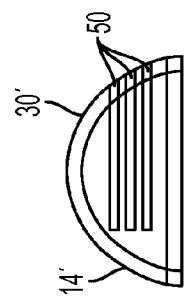
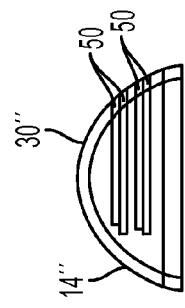
FIG. 4
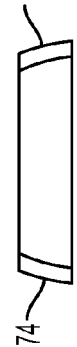
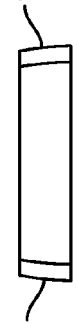
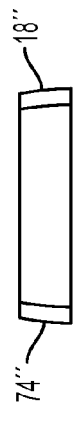
FIG. 5
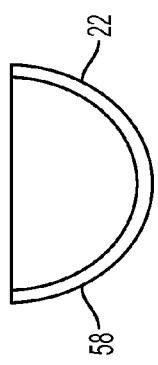
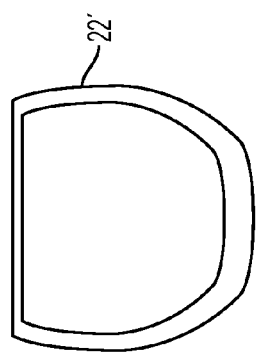
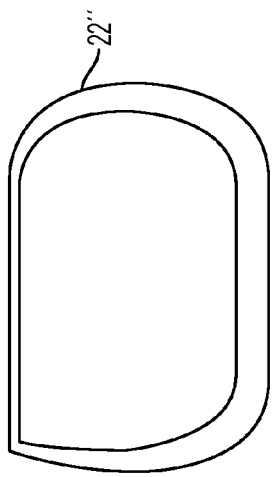
FIG. 6

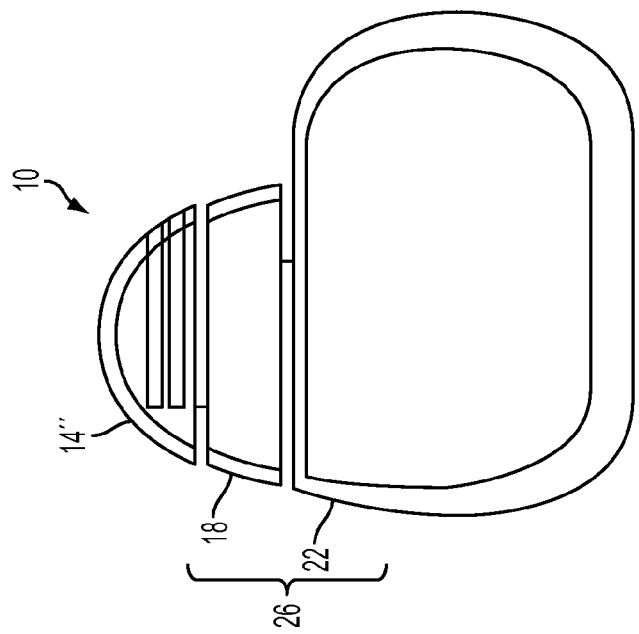
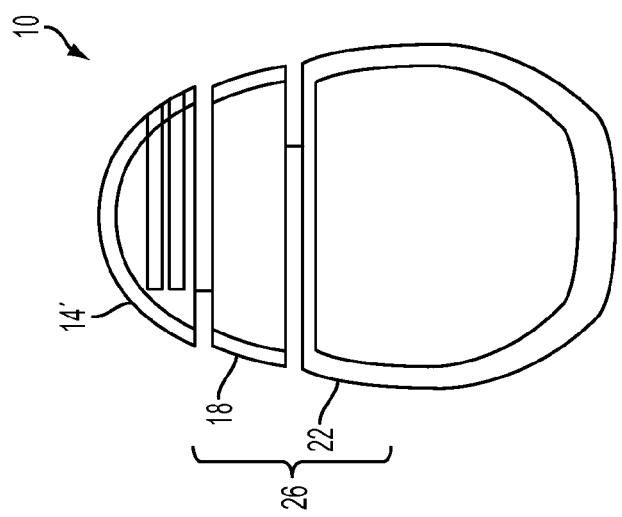
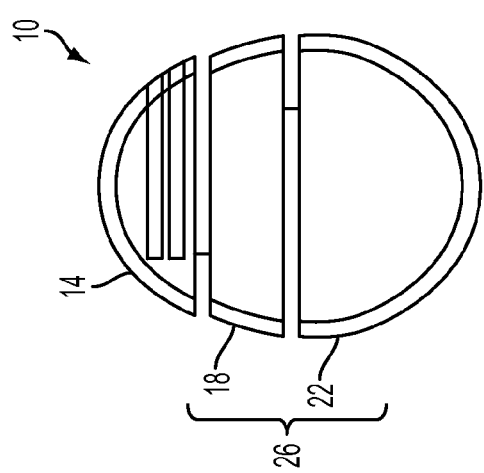

IMPLANTABLE MEDICAL DEVICE

CROSS REFERENCE TO RELATED APPLICATIONS

This application claims priority to U.S. Provisional Application No. 61/751,030, filed Jan. 10, 2013, the entire contents of which are incorporated herein by reference.

BACKGROUND

The present invention relates to an implantable medical device.

Stimulators provide therapy for a variety of treatments. A stimulator includes a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

SUMMARY

In one embodiment, the invention provides an implantable medical device including a first generator. The first generator includes a first power source coupled to a first controller. The first header is removably coupled to the first generator and includes a first lead configuration. The device includes a first lead with a lead body having first terminals and at least one electrode on an end opposite the first terminals. The first terminals are removably received and secured by the first lead configuration of the first header and configured to communicate with the first generator.

In another embodiment the invention provides an implantable medical device kit including a first generator and a second generator. The first generator includes a first power source and a first controller and the second generator includes a second power source and a second controller. A header is configured to be removably coupled to each of the first generator and the second generator. A lead includes a lead body having terminals on a first end and at least one electrode on a second end opposite the first end. The terminals are removably secured to the header and configured to communicate with each of the first generator and second generator.

In another embodiment the invention provides an implantable medical device kit including a generator with a power source and a controller. The device kit further includes a first header and a second header. The first header includes a first lead configuration for removably receiving and securing first terminals of a first lead. The first lead includes at least one electrode on an end opposite the first terminals and is configured to communicate with the generator. The second header includes a second lead configuration for removably receiving and securing second terminals of a second lead. The second lead includes at least one electrode on an end opposite the second terminals and is configured to communicate with the generator. Each of the first header or the second header is configured to be removably coupled to the generator.

Other aspects of the invention will become apparent by consideration of the detailed description and accompanying drawings.

BRIEF DESCRIPTION OF THE DRAWINGS

FIG. 4 illustrates the header of FIG. 1, the header of FIG. 2, and another header.

FIG. 5 illustrates the controller of FIG. 1, the controller of FIG. 2, and another controller.

FIG. 6 illustrates the power source of FIG. 1, the power source of FIG. 2, and another power source.

FIGS. 7A-9D illustrate implantable electrical stimulation devices each including one of the headers of FIG. 5 communicatively coupled to a generator including one of the controllers of FIG. 5 and one of the power sources of FIG. 6.

DETAILED DESCRIPTION

Figure 1:
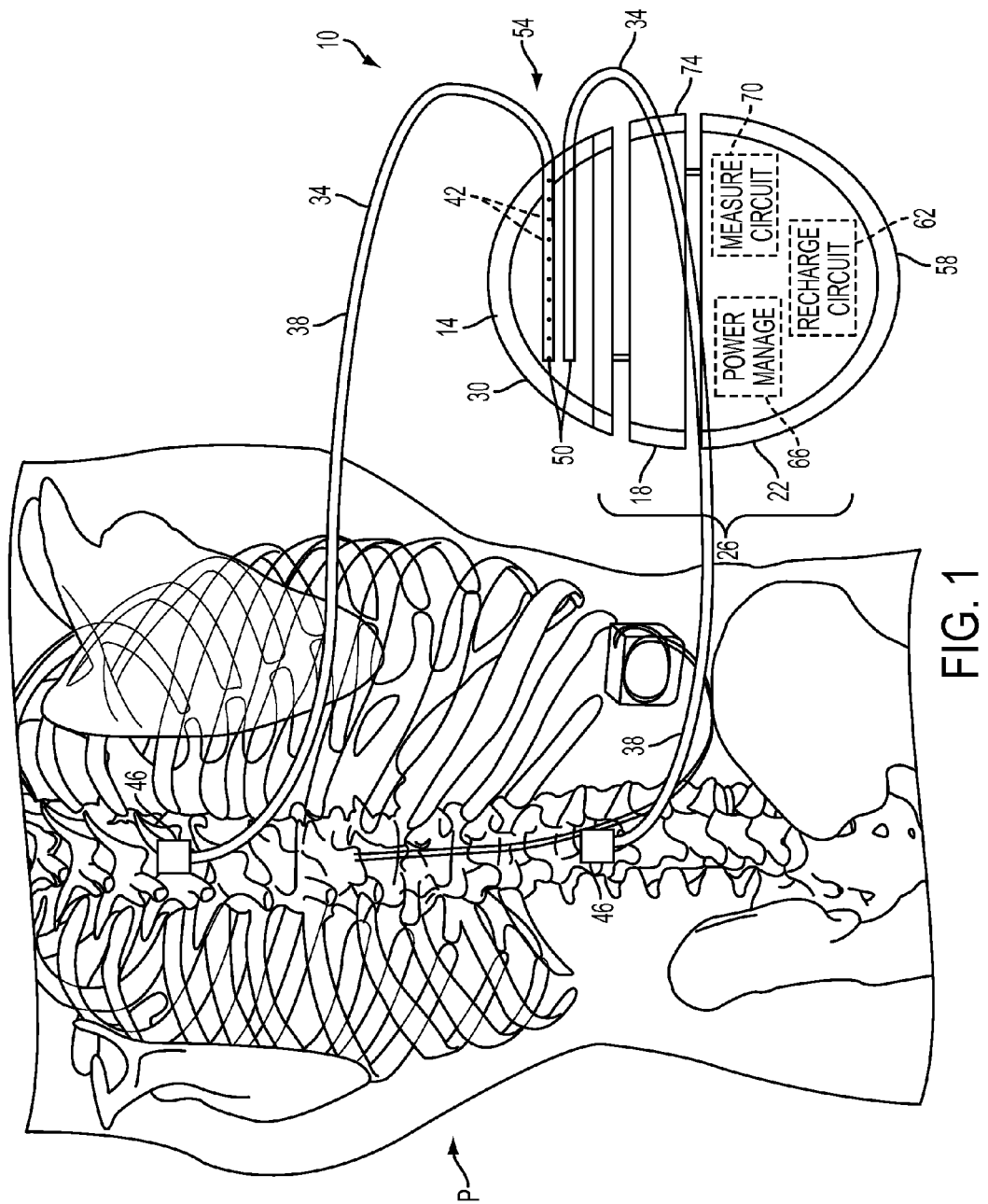
FIG. 1 illustrates an implantable electrical stimulation device including a header, a controller, and a power source according to a first embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 1-9 illustrate an electrical stimulation device 10. The electrical stimulation device includes a header 14, a core unit or controller 18, and a power source 22 (e.g., a battery unit). In the embodiment illustrated in FIG. 1A, the header 14 is removably coupled to and communicates with the controller 18. Similarly, the power source 22 is removably coupled to and communicates with the controller 18. When mechanically and communicatively coupled, the controller 18 and the power source 22 define a generator 26. As such, the header 14, the controller 18, and the power source 22 are distinct structures that are removable from one another. Additionally, each of the header 14, the controller 18, and the power source 22 are interchangeable with replacement or alternative headers 14, controllers 18, and power source 22.

Figure 2:
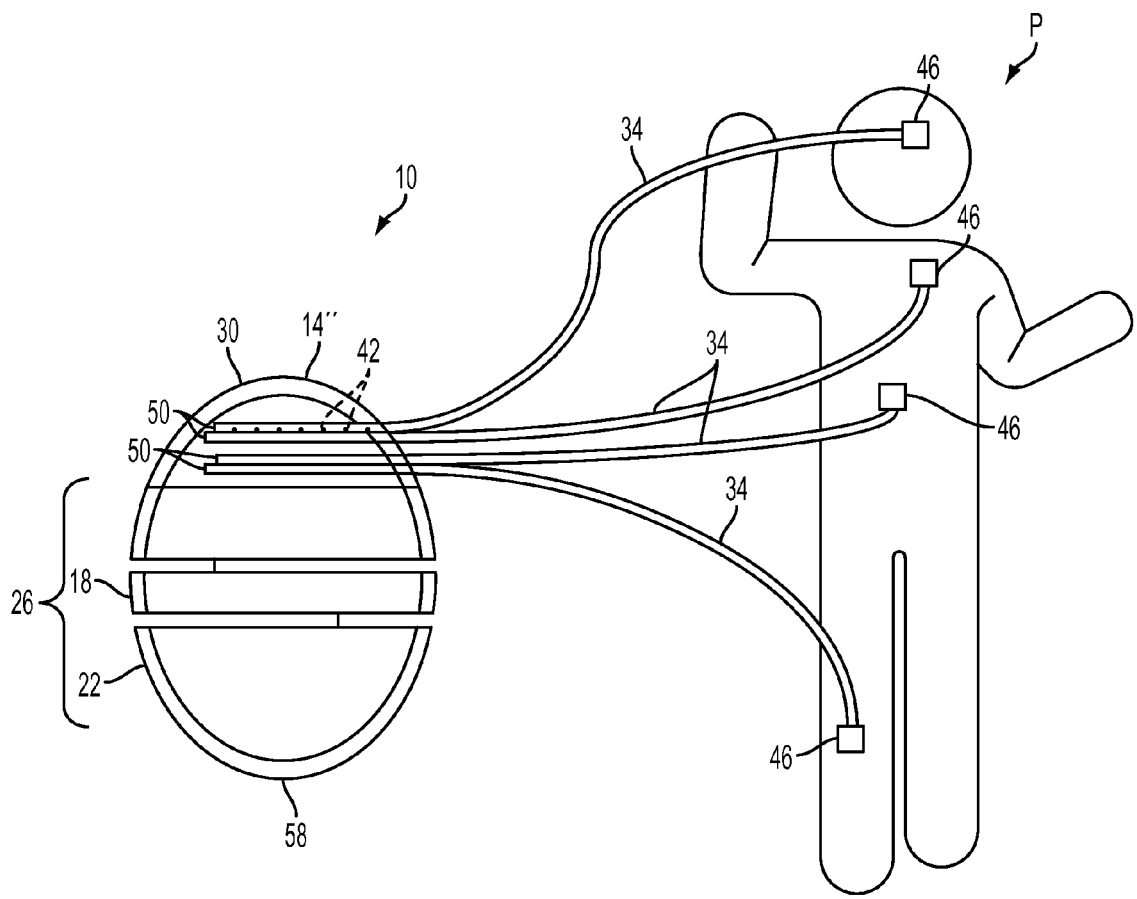
FIG. 2 illustrates an implantable electrical stimulation device including a header, a controller, and a power source according to another embodiment of the invention.

The header 14 includes a header housing 30 configured to removably secure at least one lead 34. Each lead 34 includes a lead body 38 including a first end having terminals 42 and a second end, which is opposite the first end, having an electrode 46. The header housing 30 defines at least one aperture 50 into which the first end is be inserted, as shown by directional arrow 54. The header housing 30 also includes a plurality of contacts (not shown) disposed within the aperture 50. When the lead 34 is inserted into the aperture 50, the contacts can be aligned with the terminals 42 on the lead 34 such that the controller 18, which communicates with the header 14, is in communication with the electrode 46 disposed at a second end of the lead 34. In the embodiment of FIG. 1, the header 14 of device 10 includes two apertures 50 such that two leads 34 may be removable secured to the header 14. In the embodiment of FIG. 2, the header 14" includes four apertures 50' such that four leads 34 may be removably secured to the header 14. While the headers 14, 14" are illustrated to accommodate two leads 34 and four leads 34, it should be understood that the headers 14, 14" may be configured to accommodate any number of leads 34.

The power source 22 is a battery pack including a housing 58. The power source 22 may include recharge circuitry 62 that is configured to recharge the battery. Additionally or alternatively, the power source 22 may include power management circuitry 66 that is configured to manage the power output of the battery pack. The power source 22 may also be configured via measurement circuitry 70 (i.e., sensors and the like) to measure voltages, currents or temperatures associated with the battery, or rates of change of these parameters, and control recharging and discharging according to the measured values.

Figure 3:
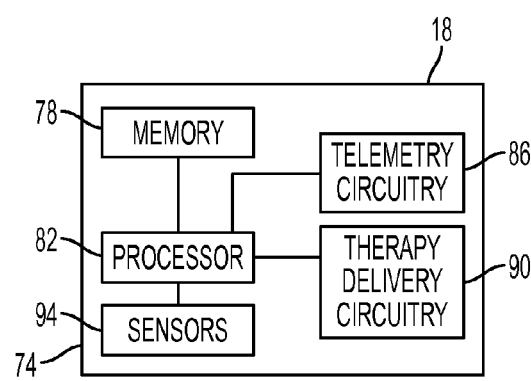
FIG. 3 illustrates the controller of FIG. 1.

The controller 18 includes a housing 74 and is configured, when coupled to and powered by the power source 22, to deliver pulses of energy to the patient P via communication with the header 14 and the leads 34. FIG. 3 illustrates several capabilities of the controller 18, although the controllers illustrated herein are merely exemplary and therefore may include alternative functionalities. In the illustrated embodiment, the controller 18 includes circuitry 78 configured to store (i.e., in a read-only memory (ROM), random access memory (RAM), electronically-erasable programmable ROM (EEPROM), flash memory, etc.) instructions for controlling the stimulation device. Data collected while the device 10 is in use may also be stored for further analysis. The controller 18 may also include a processor 82 such as a microprocessor. For example, the microprocessor may be one of a digital signal processor, an application specific integrated circuit, a field-programmable gate array, or other logic circuitry. The controller 18 also includes telemetry circuitry 86, which enables processor 82 to communicate with other devices (i.e., the header 14 and the power source 22 or external programming device via radio-frequency communication). The stimulation device delivers 10 electrical stimulation, and more particularly, the controller 18 includes therapy delivery circuitry 90 within housing 74 that generates electrical stimulation. For example, the therapy delivery circuitry 90 comprises circuits for the generation of electrical stimulation in the form of pulses, such as capacitors and switches. The controller 18 may also include sensors 94 that inform the device 10 of conditions of the patient P (i.e., position sensors, heart rate sensors, blood pressure sensors, temperature sensors, pH sensors, etc.).

As discussed above, the stimulation device 10 is configured such that the controller 18 communicates with the both the header 14 and the power source 22 to supply electrical stimulation through the leads 34 to the patient P. However, the header 14, the controller 18, the power source 22 and the leads 34 are each distinct features that are removable and replaceable from one another while implanted in the body of the patient P.

For example, FIG. 5 illustrates three different headers 14, 14', 14" each having a different configuration. In the illustrated headers of FIG. 5, the headers 14, 14', 14" differ in the number of leads 34 that are connectable thereto. For example, the headers 14 and 14", as described above receive and removably secure two and four leads 34, respectively. The header 14' includes three apertures for receiving and removably securing three leads 34. Each of the headers 14, 14', 14" may have a different lead configuration to accommodate leads having various terminal configurations. The headers 14, 14', 14" also differ in the size and relative shape. It should be understood that the headers 14, 14', 14" provided herein are merely exemplary and therefore, other headers 14, 14', 14" having other configurations are within the scope of the invention.

Similarly, FIG. 5 illustrates three different controllers 18, 18', 18" each having a different functionalities and capabilities. For example, controller 18 includes circuitry configured to deliver pulses based on the patient's position while controllers 18' is configured to deliver variable pulses at rates of approximately 1200 Hz and pulse width of approximately 1000 microseconds and controller 18" is capable of being programmed by an external device (not shown). It should be understood that the controllers 18, 18', 18" provided herein are merely exemplary and therefore, other controllers and alternative or additional functionality or other configurations are within the scope of the invention.

Further, FIG. 6 illustrates three different power 22, 22', 22" sources having different configurations. For example, power source 22 may have a voltage mode and an impedance mode while power source 22' is rechargeable and power source 22" is non-rechargeable. It should be understood that the power sources 22, 22', 22" provided herein are merely exemplary and therefore, other power sources 22, 22', 22" having alternative or additional functionality or other configurations are within the scope of the invention.

With continued reference to FIGS. 4-6, any of the headers 14, 14', 14" of FIG. 4 may be coupled or communicate with any of the controllers 18, 18', 18" of FIG. 5. Similarly, the power source 22, 22', 22" of FIG. 6 may be coupled or communicate with any of the controllers 18, 18', 18" of FIG. 6. Therefore, FIGS. 4-6 illustrate a modular stimulation system 100, which may be part of a complete kit, in which an implantable device 10 may include a header 14 having any suitable configuration, a controller 18 having any configuration, and a power source 22 having any configuration.

FIGS. 7-9 illustrate various implantable devices embodying the principles discussed above.

Figure 8C:
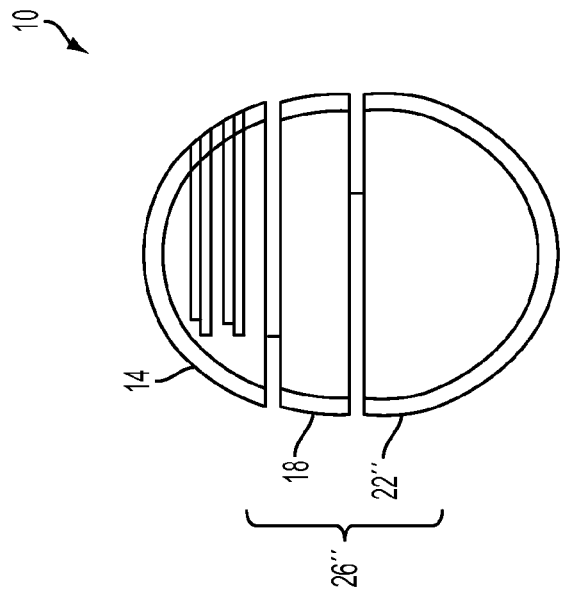
Figure 8B:
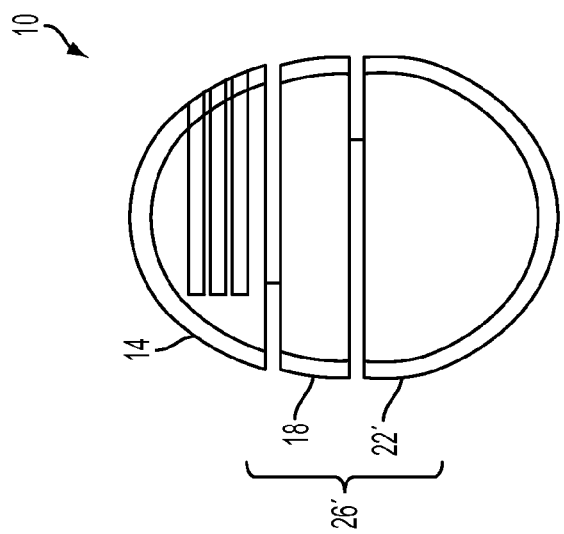
Figure 8A:
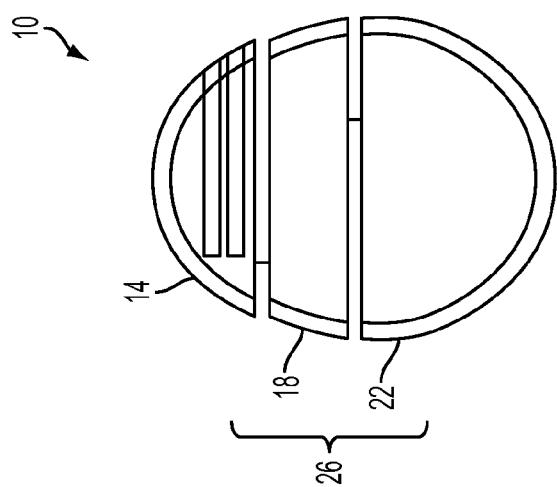
Figure 9A:
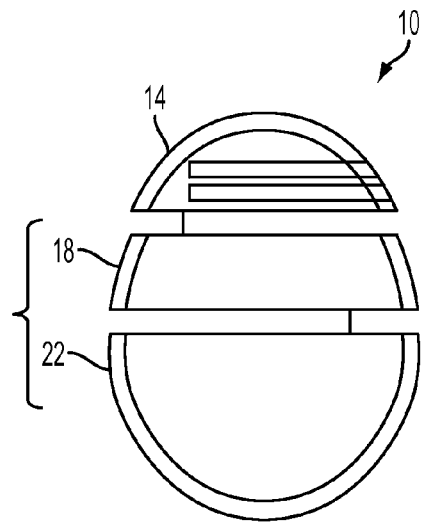
Figure 9B:
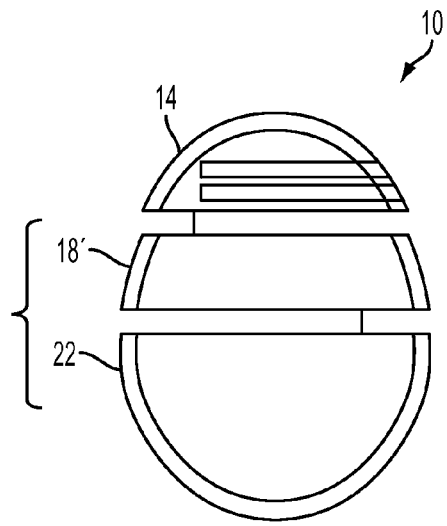
Figure 9C:
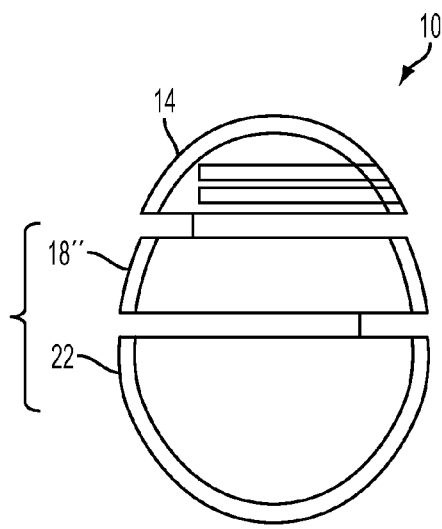
Figure 9D:
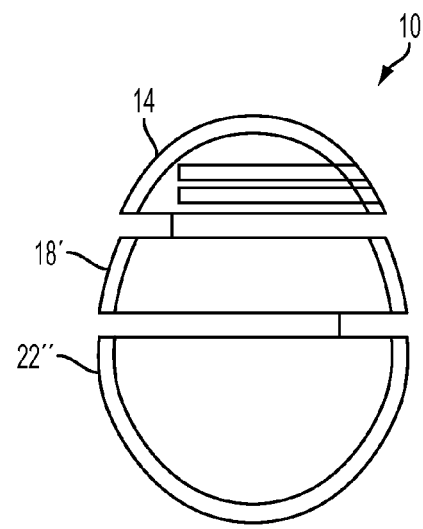

For example, FIGS. 7A, 8A, 9A illustrate an implantable device 10 that is similar to that found in FIG. 1. The device 10 includes the first controller 18 and the first power source 22 that together make up a first generator 26. The first header 14 is removably coupled to the first generator 26 and includes the first lead configuration 104 (i.e., accommodates two leads). As such the terminals 42 of the lead 34 (FIGS. 1 and 2) are removably received and secured by the first lead configuration 104 of the first header 14 and configured to communicate with the first generator 26.

FIGS. 7A-7C illustrate that the first generator 26 including the first controller 18 and the first power source 22 are capable of being decoupled from the first header 14. As such, second and third headers 14', 14" may be coupled to the first generator such that any of the headers 14, 14', 14" may be communicatively coupled to the first controller 18 of the first generator 26.

FIGS. 8-9 illustrate that the first generator 26 is removable from the first header 14 and replaceable with the second or the third generator 26' having a different configuration. In other words, both the first controller 18 and the first power source 22 can be removed and replaced (FIG. 9D) such that any type of generator may be constructed. Alternatively, as illustrated in FIGS. 8A-8C) the first power source 22 is removable from the first controller 18 and replaceable with second or third power sources 22', 22", which have other configurations. Further, as illustrated in FIGS. 9A-9C) the first controller 18 is removable from the first header 14 and the first power source 22 and replaceable with second or third controllers 18', 18", which have other configurations and capabilities. In any of the above-described embodiments, the terminals 42 of the lead 34 communicate with the any of the first, the second, and the third generators 26, 26', 26". The generator 26 may have any configuration. Therefore, the generator 26 may be constructed from a combination of any one of the first, the second, or the third controllers 18, 18', 18" with any one of the first, the second, or the third power sources 22, 22', 22". Further, the terminals 42 communicate with any of the controllers 18, 18', 18" and/or any of the power sources 22, 22', 22" that make up the first, the second and the third generators 26, 26', 26" or any other combination of controller and power source that make up the generator. Moreover, each of generators 26, 26', 26", the controllers 18, 18', 18", and the power sources 22, 22', 22" illustrated herein are interchangeable after implantation and without the entire device 10 being removed. The lead 34 is also removable from the header 14 and replaceable with a other leads 34 without removing entire device 10.

It should be understood that each lead 34 is removably coupled with the headers 14, 14', 14" by one of a direct electrical coupling, a conductive coupling, an inductive coupling, an electromagnetic induction coupling, an electrodynamic induction coupling or a resonant inductive coupling. Additionally, each of the headers 14, 14', 14" is removably coupled to the generators 26, 26', 26", and in particular the controllers 18, 18', 18", by one of a magnetic coupling, an optical coupling, a mechanical coupling, or an electrical coupling.

Figure 10:
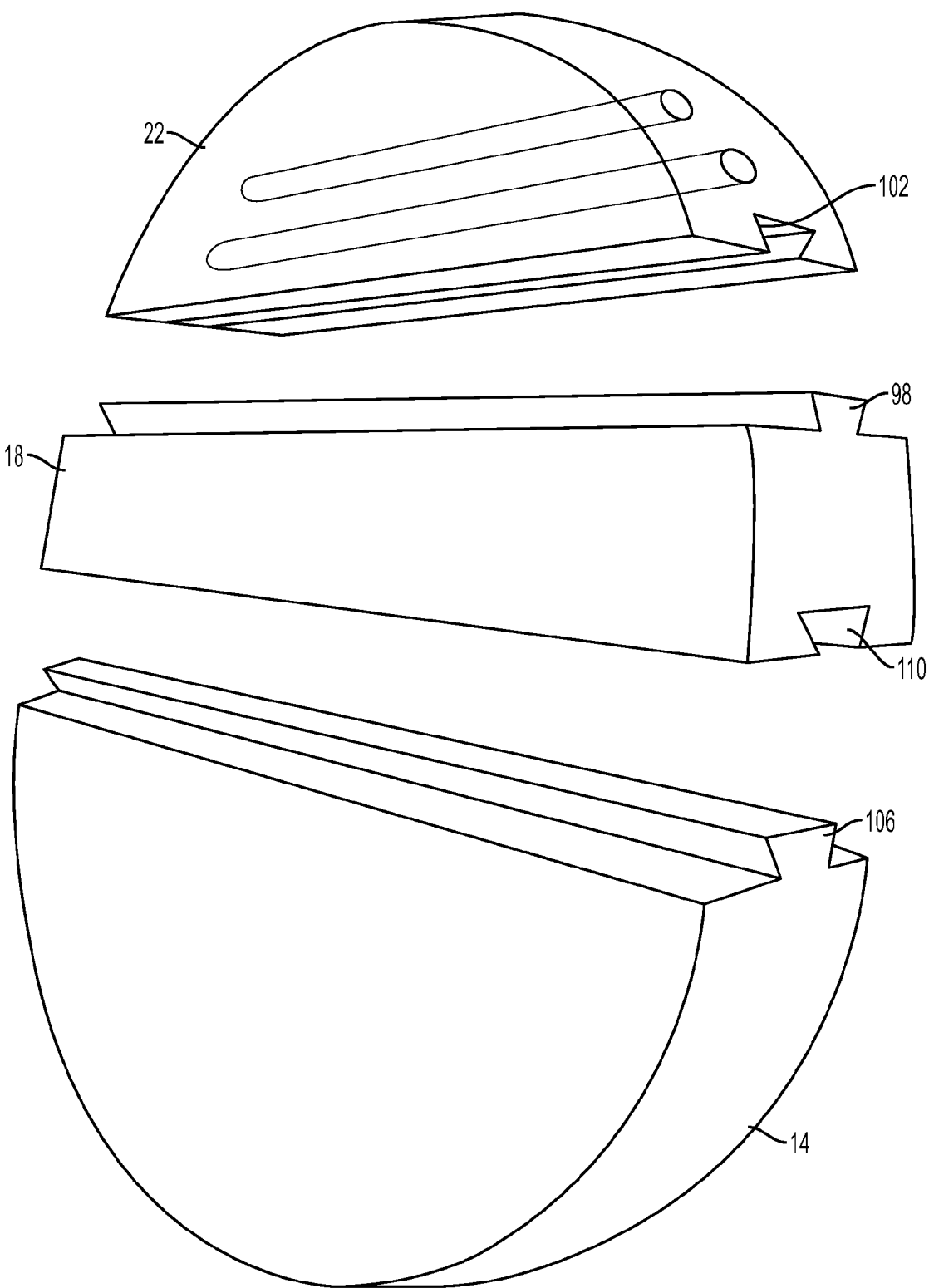
FIG. 10 illustrates an exemplary mechanical connection between the connector and each of the header and the power source of FIG. 1.

It should be understood that the headers 14, 14', 14", the controllers 18, 18', 18", and the power sources 22, 22', 22" are mechanically coupled to one another such that they remain in close proximity to one another while implanted in the patient P. FIG. 10 illustrates a device having an exemplary mechanical connection between the header 14, the controller 18, and the power source 22. In the embodiment illustrated in FIG. 10, the connector 18 includes a projection 98 that is sized and shaped to be received within a groove 102 of the header 14. Similarly, the power source 22 includes a projection 106 that is sized and shaped to be received within a groove 110 in the connector 18. The projections 98, 106 are slidable relative to and within the grooves 102, 110, respectively. The mechanical connection illustrated in FIG. 10 is merely exemplary and therefore, it should be understood that any type of mechanical connection is within the scope of the invention. Each of the header, the controller, and the power source may include snap fit interfaces or friction fit interfaces as alternative mechanical connections.

In practice and with reference to FIG. 6, a first device 10 including, for example, the first header 14 having the first lead configuration 104, the first controller 18, and the first power source 22 may be implanted into a patient P such that the leads 34 communicate between the device and the patient. As time progresses, technology advances, or the patient's needs change, it may be necessary to exchange the first header 14 with the second or third header 14', 14". Therefore, the first header 14 may be disconnected from the first generator 26 (i.e., the first controller 18) and removed from the patient P. At this point, the second or third header 14, 14" may be connected to the first generator 26 to communicate with the same. It should be understood that this process is applicable to the first controller 18 and the first power source 22 as well. That is that each of the first controller 18 and the first power 26 source may be disconnected from the device 10 and replaced with the second and the third controllers 18', 18" and power sources 22', 22", respectively. Similarly, the leads 34 may be removed and exchanged if necessary. Additionally, any combination of the header 14, the controller 18, the power source 22 and the leads 34 may be removed and replaced depending the needs of the patient and the available technology.

The modular system 100 described herein is advantageous because components (i.e., the headers, the controllers, the power sources, and the leads) of implantable devices 10 may be interchangeable for other of the same components. Therefore, components that are perfectly usable may be continued to be used for the lifespan of the component and only components that are need to be replaced need be removed and exchanged.

The electrical stimulation device 10, leads 34, and electrodes 46 are generally implanted subcutaneously. The placement of the electrical stimulation device 10 and the electrodes 46 may be positioned subcutaneously in any suitable location. Further, as discussed in detail above, the leads 34 are routed from the device 10 to the electrodes 46 to stimulate the surrounding tissue. For example, if the device 10 is used as a neurostimulator, the electrodes 46 are placed on adjacent to neural elements or structures (i.e., the brain, spinal cord, neural roots etc.) while the device 10 is positioned in the chest wall or the abdominal wall, for example.

Various features and advantages of the invention are set forth in the following claims.

What is claimed is:

1. An implantable medical device kit comprising:
   a first generator including a first power source and a first controller;
   a second generator including a second power source and a second controller, the second power source having different configuration than the first power source;
   a header configured to be removably coupled to each of the first generator and the second generator; and
   a lead including a lead body having terminals on a first end and at least one electrode on a second end opposite the first end, the terminals being removably secured to the header and configured to communicate with each of the first generator and second generator.

2. The implantable medical device kit of claim 1, wherein each of the first generator and the second generator is removable from the first header and replaceable with the other of the first generator or the second generator.

3. The implantable medical device kit of claim 1, wherein the header is removably coupled to each of the first generator or the second generator by at least one of a magnetic coupling, an optical coupling, a mechanical coupling, or an electrical coupling.

4. The implantable medical device kit of claim 1, wherein each of the first generator and second generator communicate with the lead by one of a direct electrical coupling, a conductive coupling, an inductive coupling, an electromagnetic induction coupling, an electrodynamic induction coupling, or a resonant inductive coupling.

5. The implantable medical device kit of claim 1, wherein the lead is replaceable with a second lead having terminals on a first end and at least one electrode on a second end opposite the first end, the terminals being removably secured to the header and configured to communicate with each of the first generator or the second generator.

6. The implantable medical device of claim 1, wherein the first power source is removable from the first controller and the second power source is removable from the second controller.

7. The implantable medical device of claim 6, wherein both the first power source and the second power source are configured to communicate with either the first controller or the second controller such that the first power source and the second power source are interchangeable.

8. The implantable medical device kit of claim 1, wherein the first generator and the second generator are interchangeable after implantation and without the header being removed.

9. The implantable medical device kit of claim 1 further comprising:

a third generator including a third power source and a third controller, wherein the third generator configured to be removably coupled to the first header, wherein the third generator is replaceable with each of the first generator and the second generator such that the terminals communicate with the third generator.

10. An implantable medical device kit comprising:

a header configured to permit communication between a lead and each of a first generator and a second generator, the lead including a lead body having terminals on a first end and at least one electrode on a second end opposite the first end, the terminals configured to be removably secured to the header a first implantable medical device configured to be implanted into a patient and including the first generator having a first power source and a first controller, the header removably coupled to the first generator, and the lead, the lead removably secured to the header and being in communication with the first generator;

a second implantable medical device configured to be implanted into a patient and including the second generator having a second power source having different configuration than the first power source and a second controller, the header removably coupled to the second generator, and the lead removably secured to the header and being in communication with the second generator.

11. The implantable medical device kit of claim 10, wherein each of the first generator and the second generator is removable from the first header and replaceable with the other of the first generator or the second generator.

12. The implantable medical device kit of claim 10, wherein the header is removably coupled to each of the first generator or the second generator by at least one of a magnetic coupling, an optical coupling, a mechanical coupling, or an electrical coupling.

13. The implantable medical device kit of claim 10, wherein each of the first generator and second generator communicate with the lead by one of a direct electrical coupling, a conductive coupling, an inductive coupling, an electromagnetic induction coupling, an electrodynamic induction coupling, or a resonant inductive coupling.

14. The implantable medical device kit of claim 10, wherein the lead is replaceable with a second lead having terminals on a first end and at least one electrode on a second end opposite the first end, the terminals being removably secured to the header and configured to communicate with each of the first generator or the second generator.

15. The implantable medical device of claim 10, wherein the first power source is removable from the first controller and the second power source is removable from the second controller.

16. The implantable medical device of claim 15, wherein both the first power source and the second power source are configured to communicate with either the first controller or the second controller such that the first power source and the second power source are interchangeable.

17. The implantable medical device kit of claim 10, wherein the first generator and the second generator are interchangeable after implantation and without the header being removed.

18. The implantable medical device kit of claim 10, further comprising:

a third implantable medical device configured to be implanted into a patient and including a third generator having a third power source and a third controller, the header removably coupled to the third generator, and the lead removably secured to the header and being in communication with the third generator.

19. An implantable medical device configured to be implanted into a patient, the implantable medical device comprising:

a first generator including a first power source and a first controller;

a header removably coupled to the first generator; and a lead including a lead body having terminals on a first end and at least one electrode on a second end opposite the first end, the terminals being removably secured to the header and in communication with the first generator;

wherein the first generator is removable from the header and replaceable with a second generator including a second power source having different configuration than the first power source and a second controller such that the header is removably coupled to the second generator and the lead is in communication with the second generator.

20. The implantable medical device of claim 19, wherein the first generator is removed and the second generator is implanted without removing the header and the lead.

* * * * *